United States Patent
Sama (10) Patent No.: US 12,390,638 B2
(45) Date of Patent: Aug. 19, 2025

(54) ORAL MUSCLE TRAINING

(71) Applicant: Signifier Medical Technologies Limited, London (GB)

(72) Inventor: Anshul Sama, Nottingham (GB)

(73) Assignee: Signifier Medical Technologies Limited, London (GB)

( * ) Notice: Subject to any disclaimer, the term of this patent is extended or adjusted under 35 U.S.C. 154(b) by 1147 days.

(21) Appl. No.: 16/654,616

(22) Filed: Oct. 16, 2019

(65) Prior Publication Data

US 2020/0121984 A1    Apr. 23, 2020

(30) Foreign Application Priority Data

Oct. 17, 2018  (GB) ........................... 1816882
Oct. 23, 2018  (GB) ........................... 1817217

(51) Int. Cl.

| A61N 1/36 | (2006.01) |
| A61B 5/00 | (2006.01) |
| A61B 5/03 | (2006.01) |
| A61B 5/0538 | (2021.01) |
| A61B 7/00 | (2006.01) |
| A61N 1/05 | (2006.01) |
| A63B 23/03 | (2006.01) |

(Continued)

(52) U.S. Cl.
CPC .......... *A61N 1/3601* (2013.01); *A61B 5/0088* (2013.01); *A61B 5/038* (2013.01); *A61B 5/0538* (2013.01); *A61B 5/682* (2013.01); *A61B 7/003* (2013.01); *A61N 1/0548* (2013.01); *A61N 1/36031* (2017.08); *A63B 23/032* (2013.01); *G16H 20/40* (2018.01); *A61B 5/4818* (2013.01); *A61N 1/0452* (2013.01)

(58) Field of Classification Search
CPC ...... A61N 1/3601; A61N 1/0548; A61F 5/566
See application file for complete search history.

(56) References Cited

U.S. PATENT DOCUMENTS

| 5,190,053 A | 3/1993 | Meer |
| 5,265,624 A | 11/1993 | Bowman |

(Continued)

FOREIGN PATENT DOCUMENTS

| CA | 2477540 A1 | 5/2000 |
| CN | 101590302 | 12/2009 |

(Continued)

OTHER PUBLICATIONS

Joerg Steier, Chest, Original Research, Sleep Disorders; Continuous Transcutaneous Submental Electrical Stimulation in Obstructive Sleep Apnea.

(Continued)

*Primary Examiner* — William J Levicky
(74) *Attorney, Agent, or Firm* — Shay Glenn LLP (57) ABSTRACT

A device (100) for training oral muscle tone, the device (100) includes a mouthpiece (103) having a first and second arm (131) diverging away from one another and each carrying at least one electrode means (132a, 132b, 133a, 133b), at least one of the at least one electrode means protruding proud of adjacent portions of the arms (131), electrical circuitry operatively connected to the electrode means (132a, 132b, 133a, 133b), at least one of the at least one electrode means comprising an electrically conductive polymeric or plastics material.

14 Claims, 2 Drawing Sheets

(51) Int. Cl.
*G16H 20/40* (2018.01)
*A61N 1/04* (2006.01)

(56) References Cited

U.S. PATENT DOCUMENTS

| | | | |
|---|---|---|---|
| 5,284,161 | A | 2/1994 | Karell |
| 5,490,520 | A | 2/1996 | Schaefer |
| 6,212,435 | B1 | 4/2001 | Lattner et al. |
| 8,744,589 | B2 | 6/2014 | Bolea et al. |
| 9,717,904 | B2 | 8/2017 | Simon et al. |
| 9,833,613 | B2 | 12/2017 | Sama |
| 10,058,701 | B2 | 8/2018 | Sama |
| 10,463,850 | B2 | 11/2019 | Fisk et al. |
| 10,561,836 | B2 | 2/2020 | Sama |
| 10,596,366 | B2 | 3/2020 | Sama |
| 10,646,319 | B2 | 5/2020 | Johansson et al. |
| 2003/0003422 | A1* | 1/2003 | Pasquantonio .......... A61N 1/32 433/32 |
| 2005/0038485 | A1 | 2/2005 | Ludwig et al. |
| 2007/0123950 | A1 | 5/2007 | Ludlow et al. |
| 2007/0173893 | A1 | 7/2007 | Pitts |
| 2009/0048647 | A1 | 2/2009 | Tingey |
| 2009/0210032 | A1* | 8/2009 | Beiski .................. A61N 1/0548 264/16 |
| 2010/0087893 | A1 | 4/2010 | Pasquet |
| 2010/0087896 | A1 | 4/2010 | McCreery |
| 2010/0204747 | A1 | 8/2010 | Lindquist et al. |
| 2011/0112601 | A1 | 5/2011 | Meadows |
| 2011/0155143 | A1 | 6/2011 | Shantha |
| 2013/0118504 | A1 | 5/2013 | Hermanson et al. |
| 2014/0093832 | A1* | 4/2014 | Nemeh ................ A61N 1/0548 433/1 |
| 2014/0135868 | A1 | 5/2014 | Bashyam |
| 2014/0277323 | A1 | 9/2014 | Tingey |
| 2015/0093716 | A1* | 4/2015 | Fulton, III ............... A61B 1/32 433/140 |
| 2015/0142120 | A1 | 5/2015 | Papay |
| 2015/0190630 | A1 | 7/2015 | Kent et al. |
| 2016/0106976 | A1 | 4/2016 | Kucklick |
| 2016/0158093 | A1 | 6/2016 | Amblard et al. |
| 2016/0317803 | A1* | 11/2016 | Sama .................... A61N 1/0548 |
| 2017/0143257 | A1 | 5/2017 | Kent et al. |
| 2017/0143259 | A1 | 5/2017 | Kent et al. |
| 2017/0143960 | A1 | 5/2017 | Kent et al. |
| 2017/0224987 | A1 | 8/2017 | Kent et al. |
| 2017/0312117 | A1 | 11/2017 | Shah et al. |
| 2018/0036531 | A1 | 2/2018 | Schwarz et al. |
| 2020/0121921 | A1 | 4/2020 | Sama |
| 2020/0121924 | A1 | 4/2020 | Sama |
| 2020/0164205 | A1 | 5/2020 | Sama |
| 2020/0346016 | A1 | 11/2020 | Caparso et al. |
| 2022/0296890 | A1* | 9/2022 | Tripathi ............... A61N 1/0548 |

FOREIGN PATENT DOCUMENTS

| | | |
|---|---|---|
| CN | 101596340 A | 12/2009 |
| CN | 102548610 A | 7/2012 |
| CN | 102686271 A | 9/2012 |
| EP | 0122102 | 10/1984 |
| EP | 1365832 | 10/2019 |
| GB | 1038829 | 8/1966 |
| JP | 2000511087 A | 8/2000 |
| JP | 2014 158607 | 9/2014 |
| JP | 2015093133 A | 5/2015 |
| RU | 2223798 | 2/2004 |
| RU | 2457006 | 7/2012 |
| TW | 201505682 | 2/2015 |
| TW | 615168 | 2/2018 |
| TW | I615168 B | 2/2018 |
| WO | 1992/015364 | 9/1992 |
| WO | 1997018854 | 5/1997 |
| WO | 2000029063 | 5/2000 |
| WO | 2002/066111 | 1/2002 |
| WO | WO2005/072821 A1 | 8/2005 |
| WO | 2006001644 | 1/2006 |
| WO | 2008/100779 | 8/2008 |
| WO | WO2009/127947 A2 | 10/2009 |
| WO | WO2013/144710 A1 | 10/2013 |
| WO | WO2020/081831 A1 | 4/2020 |
| WO | WO2022/118028 A1 | 6/2022 |

OTHER PUBLICATIONS

Tripathi; U.S. Appl. No. 18/328,670 entitled "Oral muscle composition detection and training," filed Jun. 2, 2023.

* cited by examiner

ORAL MUSCLE TRAINING

This invention relates generally to oral muscle training, particularly to oral muscle training devices, methods, systems and control software. More specifically, although not exclusively, this invention relates to the training of muscles of the mouth for the treatment of sleep disordered breathing.

Snoring and sleep apnoea are considered as part of a range of conditions often termed as sleep disordered breathing (SDB), with symptoms relating to disordered breathing patterns during sleep. SDBs are not only a nuisance, but they can also result in health problems, for example frequent waking from sleep, light sleeping, strain on the heart, low oxygen levels in the blood, headaches and fatigue.

The breathing passage of humans between the throat, back of the nose and mouth, to the level of the larynx, is a collapsible tube. It has been observed that collapse of the breathing passage occurs at a positive airway pressure in individuals who snore and/or suffer from sleep apnoea syndrome and at a negative airway pressure in individuals who do not.

In an effort to address this phenomenon, treatments have been developed which include using a continuous positive airway pressure device to keep the breathing passage open or wearing a mandibular advancement device to hold the jaw and tongue forward in order to increase the space at the back of the throat.

These devices can cause discomfort such as a dry throat, they address the symptoms only temporarily, rather than addressing the underlying cause, and they must be used during sleep on an ongoing basis. As a result, users find it difficult to fall asleep or remain asleep and compliance is therefore low. Therefore, it is desirable to provide a treatment that does not require the regular use of such devices during sleep and that addresses the underlying cause for the condition.

Recent research studies have shown that implanting electrical nerve stimulators into the mouth are effective in the treatment of obstructive sleep apnoea. This involves intrusive surgery to implant sensors and electrodes on nerves in these areas. The device identifies an episode of obstruction using the sensors and stimulates the tongue nerve to cause contraction to relieve the obstructive event. As with pacemakers, this approach leads to maintenance and other complications, such as battery replacement, risks associated with electrical fields and issues related to external security detection devices. In addition, stimulation only occurs during an obstructive episode during sleep; it does not address the underlying cause of the condition.

It is also known to provide intraoral electrical stimulation devices comprising electrodes provided on a mouthpiece, for example, as described in US2014/0135868. The device is provided with electrode configurations for contacting the genioglossus muscle towards the floor of the mouth. It is intended that the device is for use during sleep to continuously stimulate the muscle, or synchronised to the intrinsic respiratory cycle, or in response to an apnoea episode. Because the device is intended to be worn during the night when the wearer is asleep it is necessary to provide a retainer to ensure that the device remains in place.

US2014/0135868, and devices similar thereto, are reactive rather than proactive, meaning that they intended to activate when an incident of sleep disordered breathing such as snoring occurs. Consequently, these prior art devices are not aimed at training muscle tone.

One of the major issues with asking patients to wear devices during the night is one of compliance. The devices are unsightly, can be uncomfortable to wear and efficacy may be difficult for the wearer to detect. In addition, it is often the case that retainer devices must be manufactured to conform to the geometry of a particular user's mouth, for example, by taking dental impressions to produce a cast or model, from which the device may be fabricated. This is a cumbersome and time-consuming process.

In other reactive devices, electrodes may be implanted into the tissue of a patient's mouth, as described in US2007/0173893. Such surgical interventions are expensive, permanent and may well be uncomfortable.

In our earlier patent, U.S. Pat. No. 9,833,613, we disclose a device for the treatment of SDB wherein a user is able to train muscles of the mouth to improve muscle tone and thereby stop, or at least inhibit, SDB events. The user will typically apply the device whilst in an awake state to improve muscle tone. In one embodiment the device has a mouthpiece for location between the upper and lower mandibular arches and a pair of flanges for engaging the upper or dorsal surface of the tongue and a pair of flanges for engaging the sublingual surface of the tongue, each of the flanges including an electrode. Energising the device causes an electric current to be applied to the tongue to improve tongue muscle tone.

It is a first non-exclusive object of the invention to provide an "over-the-counter" treatment system, preferably to be used in an awake state, that provides a sustainable reduction in disordered breathing patterns during sleep. Clearly, for an "over the counter" treatment system it is important that the components do not require bespoke fabrication for each patient. It is a further, more general object of the invention to provide a treatment system and device that is more effective in at least one respect than existing systems and devices for the treatment of SDBs.

Accordingly, a first aspect of the invention provides a retainer-less device for training oral muscle tone, the device comprising a mouthpiece having a pair of arms diverging away from one another and each carrying at least one electrode means, the at least one electrode means protruding proud of adjacent portions of the arms, electrical circuitry operatively connected to the electrode means, the at least one electrode means comprising an electrically conductive plastics material. Preferably the device is configured to provide, in use, via the electrode means electrical stimulation to one or more oral muscles to increase resting muscle tone and/or muscle tone during sleep.

In embodiments, the plastics material may comprise or consist of a polymeric material, e.g. silicone and/or polyurethane polymer. Other plastics or polymeric materials may be used.

The arms may be joined. Each of said arms may have a longitudinal axis and comprise a flange extending as a continuation of the longitudinal axis from a free end of the arm. Preferably each flange may carry said at least one electrode means.

A further aspect of the invention provides a device for training oral muscle tone, the device comprising a mouthpiece having joined first and second arm diverging away from one another, each of said first and second arms having a longitudinal axis and having a flange extending as a continuation of the longitudinal axis from a free end of the arm, each flange carrying an at least one electrode means, at least one of the at least one electrode means protruding proud of adjacent portions of the flange, electrical circuitry operatively connected to the electrode means, at least one of the said at least one electrode means comprising an electrically conductive plastics material.

Preferably, the flanges extend towards one another. It will be appreciated that having the flange extend from a free-end of each arm the dorsal surface of the tongue can be contacted, preferably a posterior portion of the dorsal tongue surface. The effect is enhanced when the flanges extend towards one another.

The device is preferably free or a retainer or is retainer-less.

In this specification a retainer is a component which is secured or securable to a person's mandibular arch or a portion thereof. Retainers may be in the form of, for example, a dental tray or impression tray which may be provided with wires, or clips, or wires which are arranged to allow securement within the oral cavity. Simple retainers may comprise a mouthpiece which has a top wall and two facing walls extending therefrom to embrace a person's teeth to effect securement within a wearer's mouth.

It has been found that by arranging the electrode means to protrude proud of the adjacent mouthpiece, improved contact between the electrode means and an inner surface of a user's mouth can be achieved. In such a case, the electrode means are not obstructed by the mouthpiece, or suffer from a reduced level of obstruction.

The electrical circuitry may be formed from an electrically conductive plastics material. Alternatively, the electrical circuitry may be formed from metal wires.

The said one or more electrode and/or the electrical circuitry may be formed from an electrically conductive silicone plastics material.

In embodiments, the pair of arms may be joined at one end thereof, for example a proximal end. Each of the pair of arms may diverge towards a second end, for example a distal end.

The arms are elongate and, during use, are located between the upper and lower mandibular arches of the user. There is no overhang from the arms along or over the teeth of the user.

The electrical circuitry may extend along the arms. The arms may be formed from a flexible material, for example, a polymeric or plastics material, e.g. a silicone plastics material.

It has been further found that by providing arms fabricated from a flexible material, and/or by providing the electrode means and/or the electrical circuitry as electrically conductive plastics material affords the device an enhanced degree of flexibility/conformability. In such a case, the device can more easily conform to the geometry of a user's mouth. By having a more conformable and/or flexible device it is possible to supply it "over-the-counter" because it is a "one-size-fits-all" (or at least 'one size fits many') device. This is beneficial if the device is sold 'over-the-counter' (e.g. on the internet or from a high-street shop) because a device can be provided in, say, small medium and large sizes and each one may be used by many users, even with different shaped mouths/mandibular arches/teeth and so on. In contrast, those prior art devices which require retainers which embrace the teeth (or those devices which are secured to the teeth of a user) need the intervention of a trained dentist, or other trained person, to size and/or fit the device and/or suffer from an issue of conformability.

Further, when the arms of the device are formed from a flexible material (e.g. a silicone material) the device may be more comfortable to wear during treatment periods. Because the electrodes are formed of a conductive plastics material which protrudes beyond the adjacent arm portions they are able to conform to the user with the required resilience to provide an effective contact, in use.

Each of the pair of arms may comprise one or more flanges or appendages extending therefrom, for example opposite one another.

The one or more appendages or flanges may extend inwardly of the pair of arms, e.g. from one arm and toward the other arm. In embodiments, each arm comprises two or more appendages or flanges, for example an appendage or flange extending from a free end of each arm and/or an appendage or flange extending from an intermediate portion of each arm.

At least one or each of the appendages or flanges may comprise or carry said one or more electrode means, for example one or more electrodes, or series thereof. At least one electrode means or series of electrodes may be adjacent and/or associated with and/or exposed at a surface, e.g. a major surface, of the at least one appendage or flange. In embodiments, at least one of the appendages or flanges comprises electrode means associated with each of its major surfaces. The one or more flanges or appendages may carry at least one electrode means that may protrude or stand proud of an adjacent or associated appendage or flange, for example a surrounding area thereof.

In embodiments, each of the pair or arms may comprise a pair of flanges or appendages, e.g. a first flange or appendage and a second flange or appendage extending therefrom.

Each of the pair of flanges, for example the first flange or appendage and second flange or appendage, may comprise a respective electrode means protruding proud of the surrounding area of the respective flange or appendage. The first flange or appendage may comprise a first electrode protruding proud of the surrounding area of the first flange. The second flange or appendage may comprise a second electrode protruding proud of the surrounding area of the second flange.

Because the electrode means stand proud of the adjacent portion of the device, the contact surface area can be high. This means that even if the resistance of the electrode is higher than for a metal electrode, the electrode is effective.

Optionally, at least one electrode means of each respective arm or flange, for example each respective opposing flange, may be arranged, in use, to be located or locatable either side of a midline of the face of a user.

The pair of arms may together describe a horseshoe shape or V-shape or U-shape. The pair of arms may extend at least partially alongside each other and/or at an angle relative to one another and/or parallel to each other.

At least one appendage, flange or electrode means may be curved, e.g. a flat curved shape or member, and/or extend upwardly or downwardly or out of the plane of the mouthpiece or at least one arm thereof. At least one appendage, flange or electrode means may be shaped to cooperate or approximate or accommodate a tongue surface, for example a dorsal tongue surface or a sublingual tongue surface. In embodiments, the mouthpiece comprises at least one appendage, flange or electrode means that is shaped to cooperate or approximate or accommodate a dorsal tongue surface and at least one appendage, flange or electrode means that is shaped to cooperate or approximate or accommodate a sublingual tongue surface.

In embodiments having a pair of flanges or appendages, one of the pair may be shaped to cooperate or approximate or accommodate a dorsal tongue surface and the other of the pair may be shaped to cooperate or approximate or accommodate a sublingual tongue surface.

In embodiments, the at least one flange or appendage (e.g. a pair of flanges or appendages) may be formed from a flexible material, for example, a plastics material, e.g. a silicone plastics material.

Advantageously, the provision of the at least one flange or appendage being fabricated from a flexible material enables the device to be conformable to provide a "one-size-fits-all" device.

In an embodiment the device may have overall dimensions, in plan from above of length 70 to 95 mm, for example 75 to 85 mm, width 45 to 65 mm, say 50 to 60 mm and height 15 to 30 mm, say 18 to 26 mm. In an embodiment the dimensions of the device are A=15-18 mm, B=50-55 mm, C=25-28 mm, D=18-22 mm, E=15-25 mm, F=50-60 mm (the letters A to F being as shown in the drawings). Accordingly, the maximum width dimension (F) of the device may be from 45 to 65 mm. The maximum length footprint of the arms and associated flanges (B) may be from 45 to 65 mm. The, some or each electrode will typically protrude from the surrounding, adjacent surface of the mouthpiece, for example the surrounding adjacent surfaces of the flange by 0.5-5 mm, say from 1 to 4 mm. The arms may be sufficiently flexible to allow the flanges (e.g the terminal flanges at the end of the arms) to be brought into abutment or contact.

The electrode means associated with one of the major surfaces a flange or appendage may be isolated and/or controllable independently from another or the other major surface thereof. Additionally or alternatively, the electrode means of or associated with one appendage or flange may be isolated and/or controllable independently from at least one other appendage or flange.

In embodiments, the mouthpiece is formed from a non-electrically conductive (i.e. an electrically insulating) polymeric or plastics material, for example a silicone plastics material, for example a non-electrically conductive silicone plastics material. The silicone plastics material may comprise a silicone rubber.

In embodiments, the mouthpiece at least partially surrounds or encases the at least one electrode means and/or electrical circuitry. In some embodiments, the mouthpiece, for example the plastics material of the mouthpiece, completely surrounds or encases the electrical circuitry. The mouthpiece, for example the polymeric or plastics material of the mouthpiece, may partially surround or encase the at least one electrode means, for example such that a major surface of the at least one electrode means is exposed.

Providing a mouthpiece formed from a suitable non electrically conductive polymeric or plastics material, for example a silicone polymeric or plastics material, in addition to the electrically-conductive plastics material of the at least one electrode means, reduces the likelihood of material incompatibility between the mouthpiece and the one or more electrode means. Reducing the material incompatibility also reduces the likelihood of material separation or delamination between the mouthpiece and electrode means. This is further enhanced when the electric circuitry is also made from a polymeric or plastics material. The material of the electrodes and/or electric circuitry and/or body of the mouthpiece will preferably be formed from compatible materials such that interfacial surfaces are not at risk of delamination or failure.

Further, a mouthpiece formed from flexible polymeric or plastics materials having a degree of resilience, for example a rubber material, may be comfortable for a user to retain between the teeth of the user due to the resilience of the material.

In some embodiments, the mouthpiece comprises a shield or shield means, for example on one side of the electrode means, e.g. for inhibiting or preventing the electrical stimulation or current from being applied or provided by or at or from one side of the mouthpiece. The non-electrically conductive polymeric or plastics material, e.g. the silicone polymeric or plastics material may form or provide the shield or shield means.

The electrically conductive polymeric or plastics material, e.g. the silicone polymeric or plastics material may comprise electrically conductive silicone rubber. The electrically conductive polymeric or plastics material may comprise electrically conductive particles, for example one or more of carbon, silver, copper, gold particles. In an embodiment the electrically conductive polymeric or plastics material may comprise electrically conductive particles located within a polymeric material matrix or plastics material matrix, preferably a silicone plastics material matrix. The electrically conductive particles are located in sufficient proximity to provide electrical conductivity. The electrically conductive particles may comprise a particle coated in a conductive coating. In an embodiment the particle may comprise one or more of carbon, copper, silver or gold particles coated in a one or more of gold, silver, copper. In a particular embodiment, the conductive particles are silver-coated copper particles. The silver-coated copper particles may be located within a polymeric or plastics material matrix, for example a silicone plastics material matrix. The particles may be spherical, round, elliptical, rhomboidal, trapezoidal or other shapes. The particles may have a low aspect ratio (e.g. aspect ratio <3) or a high aspect ratio (e.g. aspect ratio ≥3). In embodiments the conductive particles may be fibres.

Advantageously, it is known that some metals have antibacterial properties. Indeed, both silver and copper are known to have antibacterial properties. Accordingly, said one or more electrode means comprising silver and/or copper may improve the antibacterial properties or the device. Such properties are advantageous in that the provision of antibacterial species will at least help to prevent the development of bacteria on the electrodes, which will be beneficial with the improved contact between the device and the inside of a user's mouth.

The mouthpiece may comprise a gripping base, which may comprise an enlarged end, e.g. an enlarged free end, which may be connected or secured to, e.g. formed integrally with, the mouthpiece or a body or one or more or each arm thereof, for example by a necked portion.

The gripping base may provide a connection means for electrically connecting the mouthpiece to a controller. The gripping base may comprise a printed circuit board assembly (PCBA). The PCBA may be flexible or rigid. The PCBA may be encapsulated in a plastics material, for example a silicone plastics material.

The or each electrode means preferably comprises at least one anode and at least one cathode, for example two or more anodes and/or two or more cathodes, e.g. a plurality of anodes and a plurality of cathodes. At least part of the electrode means, for example one or more or each or all of the electrodes, may be mounted to or on or within and/or at least partially housed or contained within the mouthpiece.

The mouthpiece may be insertable into the mouth and held in place, e.g. manually. The mouthpiece may be at least partially flattened and/or substantially flat and/or paddle-shaped, for example with at least one flat and/or major surface, preferably two flat major surfaces. In some embodiments, the device may include a handle to which the mouthpiece may be connected or mounted or attached, for example rigidly and/or releasably, e.g. to enable the mouthpiece to be inserted and/or held, in use, within one or more locations or positions and/or orientations within the mouth. In embodiments, the mouthpiece is free of any mounting means for mounting or securing it to or in or within the mouth of a user.

In embodiments, the mouthpiece may include a mounting means. The mounting means may be for mounting the mouthpiece to an upper part or portion of the mouth, for example such that he mouthpiece or the or a first side or surface thereof is or may be in contact with and/or adjacent one or more palate muscles and/or the roof of the mouth and/or the mouthpiece or the or a second side or surface thereof is or may be in contact with and/or adjacent one or more tongue muscles, for example a dorsal tongue surface. Additionally or alternatively, the mounting means may be for mounting the mouthpiece to a lower part or portion of the mouth, for example such that the mouthpiece or the or a first side or surface thereof is or may be in contact with and/or adjacent one or more tongue muscles, for example a sublingual tongue surface. In embodiments, the device comprises a first mouthpiece with mounting means for mounting it to an upper part or portion of the mouth and a second mouthpiece for mounting it to a lower part or portion of the mouth.

The device is preferably configured to provide a current, for example an electric current or impulse current, which may be selected from one or more of a Russian current, interferential current, pre-modulated current, DC electric current, biphasic electric current or impulse current. Other current forms may be used.

There is further provided, in another aspect of the invention, an apparatus comprising a device as set out above and a controller.

The controller may comprise an input means or activator, which may include one or more input devices, buttons and/or push buttons and/or switches and/or dials or the like, e.g. for enabling or activating or initiating the electrical stimulation or current. The device or handle may comprise a power source and/or a cable connectable to a power source. In some embodiments, the device comprises a main body that includes or incorporates or provides the handle and/or which includes or houses the power source, which may comprise a rechargeable power source or one or more batteries that may be rechargeable, and/or which can either include the cable or be operatively, e.g. inductively, connectable to a charging station that includes or incorporates the cable, for example to enable the power source to be recharged. The device may include the or be connectable to a charging station.

The controller may be arranged to energise said at least one electrode means.

The apparatus may comprise a control means, for example a controller, which may be programmed or programmable, for example to control one or more features of the electrical stimulation or current or currents, for example according to a predetermined treatment regime. The control means may comprise a control system and/or a controller and/or may comprise or be at least partially comprised in the electrical circuitry. The control means may comprise at least part of the adjustment means or adjuster, e.g. one or more of the frequency and/or pulse duration and/or intensity and/or amplitude and/or treatment duration adjustment means or adjusters.

A further aspect of the invention provides a method of forming a device for training one or more oral muscles, the method comprising forming one or more electrodes from an electrically conductive plastics material and providing said one or more electrodes on at least one arm of a pair of arms such that said one or more electrodes protrude beyond the adjacent surface of the arm.

The method may comprise forming electrical circuitry from an electrically conductive plastics material. In an embodiment the method comprises integrally forming electrical circuitry and said one or more electrode means from an electrically conductive plastics material.

The method may further comprise at least partially encapsulating said one or more electrode and/or said electrical circuitry within a non-electrically conductive plastics material.

The method may comprise, providing a first layer of non-electrically conductive plastics material. The method may comprises providing an electrically conductive plastics material on the first layer, the electrically conductive plastics material comprising an electrode and, in embodiments, electrical circuitry.

The method may further comprise providing a second layer of non-electrically conductive plastics material over the electrically conductive plastics material.

The method may comprise forming a body comprising at least one or more electrodes and electric circuitry from electrically conductive plastics material. The method may further comprise encapsulating the body in non-electrically conductive plastics material to leave said at least one or more electrodes exposed.

In an embodiment, the electric circuitry is connected to a PCB or PCBA.

The PCB of PCBA may be encapsulated.

In a further aspect of the invention, the method comprises forming a pair of electrodes and electrical circuitry interconnecting the electrodes from an electrically conductive plastics material and encapsulating, for example by insert moulding, the electrodes and electric circuitry in a non-electrically conductive plastics material to provide a pair of arms each comprising an electrode and wherein each of the electrodes extends proud of the adjacent portion of the arm.

For the avoidance of doubt, any of the features described herein apply equally to any aspect of the invention.

Another aspect of the invention provides a computer program element comprising and/or describing and/or defining a three-dimensional design for use with a simulation means or a three-dimensional additive or subtractive manufacturing means or device, e.g. a three-dimensional printer or CNC machine, the three-dimensional design comprising an embodiment of the apparatus described above.

A yet further aspect of the invention provides a computer readable medium having a program stored thereon, where the program is arranged to make a computer execute a procedure to implement one or more steps of the aforementioned method.

The apparatus may comprise a control means, which may be programmed or programmable, for example to control one or more features of the electrical stimulation or current or currents, for example according to a predetermined treatment regime. The control means may comprise a control system and/or a controller and/or may comprise or be at least partially comprised in the electrical circuitry. The control means may comprise at least part of the adjustment means or adjuster, e.g. one or more of the frequency and/or pulse duration and/or intensity and/or amplitude and/or treatment duration adjustment means or adjusters.

Embodiments of the invention will now be described by way of example only with reference to the accompanying drawings in which.

Figure 1A:
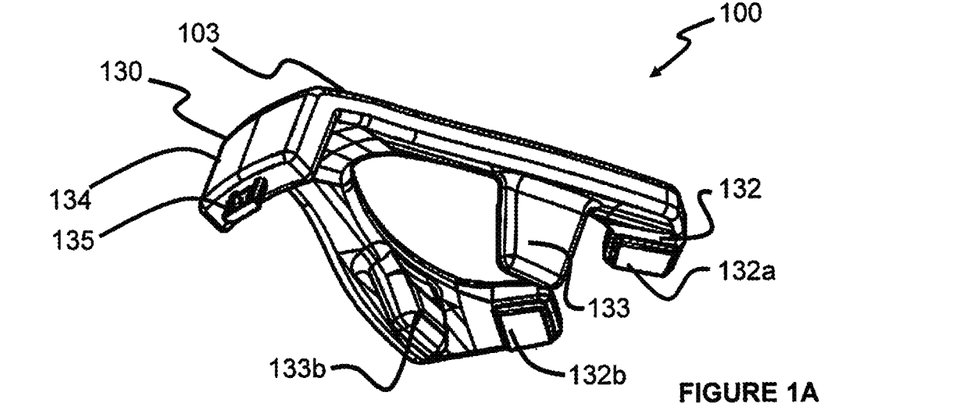
FIGS. 1A, 1B and 1C are respectively perspective, plan and side elevation views of an apparatus according to an embodiment of the invention.
Figure 1B:
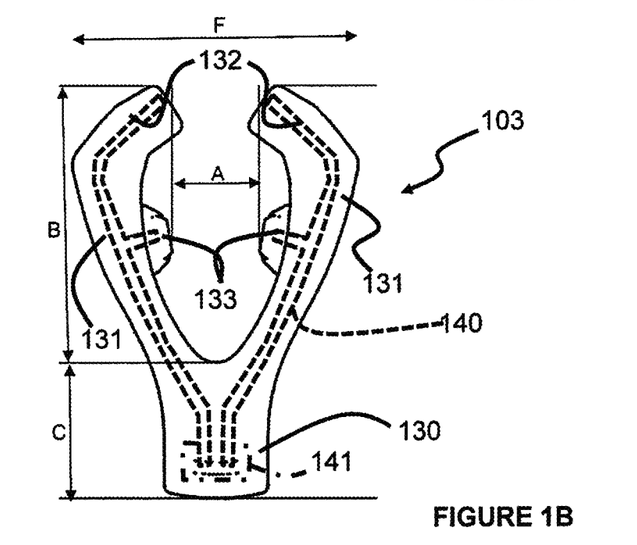
Figure 1C:
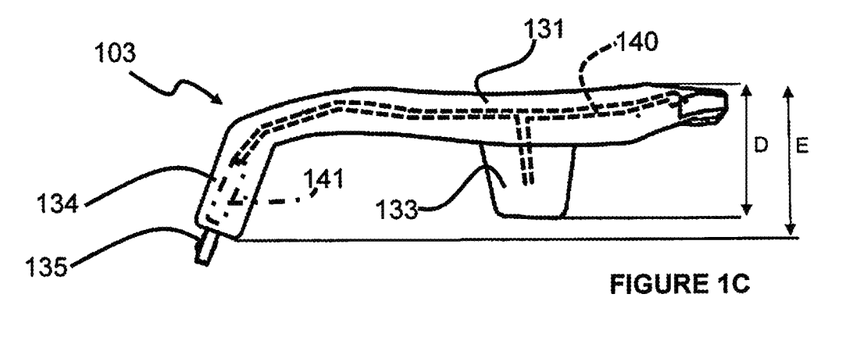

Referring now to FIGS. 1A to 1C there is shown apparatus 100 according to the invention comprising a mouthpiece 103 which includes a gripping base 130 of substantially uniform width with depending portion 134 arranged to extend over a user's bottom lip. The apparatus 100 also includes a pair of curved arms 131 formed integrally with one end of the base 130 to form a horseshoe shape. Each of the arms 131 has first and second flanges 132, 133 within which are provided electrodes (132a, b; 133a, b). The electrodes (132a, b; 133a, b) protrude proud of the adjacent portions of the associated flanges 132, 133 to facilitate good connection with the facing portion of the user's tongue, i.e. maximise the contact area and/or contact pressure between the electrodes (132a, b; 133a, b) and the user's tongue. The electrodes (132a, b; 133a, b) protrude proud of the respective flange 132, 133 formed from the material of the mouthpiece so as to be the first point of contact between the apparatus 100 and the inside of a user's mouth.

Each of the first flanges 132 and second flanges 133 are planar and have a respective electrode (132a, b; 133a, b) protruding proud from a first major surface thereof. The first flanges 132 extend inwardly toward one another from the free end of a respective one of the arms 131 and substantially on the same plane as the respective arm 131. In use the flanges 132 engage the dorsal surface 57 of the tongue. The second flanges 133 extend inwardly toward one another from an intermediate part of a respective one of the arms 131 and downwardly for accommodating the sublingual tongue surface. As looked at in a perspective view (FIG. 1A), the electrodes 132a, 132b on the first flanges 132 will face downwardly whereas those electrodes 133a, 133b on the second contact flanges 133 will face generally upwardly. In this way, with the user's tongue located between the first 132 and second 133 flanges the electrodes 132a, 132b; 133a, 133b will apply an electrical field to both the dorsal and sublingual surfaces of a user's tongue and will specifically target the genioglossus muscle.

The mouthpiece 103 also includes electrical circuitry 140 feeding the respective electrodes (132a, b; 133a, b). Each of these electrodes (132a, b; 133a, b) is electrically isolated from the others by a shielding material, thereby enabling all surrounding muscles to be stimulated simultaneously or in any sequence required. In the present embodiment, the shielding material is the material of the mouthpiece 130 and the shield provided by the shielding material is described by the body of the mouthpiece 130.

As shown, the electrical circuitry 140 is shown in schematic form.

In this embodiment, the mouthpiece 103, and therefore shielding material, is formed of a food grade or a biocompatible grade plastic material, for example made from silicone plastics material. The electrodes 132a, b; 133a, b and electrical circuitry 140 are formed of an electrically conductive silicone plastics material in this embodiment. The electrically conductive silicone plastics material is formed from electrically conductive particles embedded within a silicone matrix. In the present embodiment, the electrically conductive granules are silver coated copper granules. These provide electrical conductivity in addition to antibacterial properties.

The electrodes 132a, 132b; 133a, 133b are partially surrounded by the material of the mouthpiece 130 such that a contact surface of each of the electrodes 132a, 132b; 133a, 133b is left exposed. The electrical circuitry 140 is completely encased by the material of the mouthpiece.

Each electrode 132a, 132b; 133a, 133b is in the form of a single pad in this embodiment as it provides a large surface area. With a mouthpiece 103 in which the dimensions are A=15-18 mm, B=50-55 mm, C=25-28 mm, D=18-21 mm, the electrodes will typically protrude by 0.5-5 mm from the surrounding, adjacent surface of the flange.

The electrical circuitry 140 is connected to a printed circuit board (PCB) 141.

The terminal portion of the depending portion 134 includes an electrical connector or interface 135 for connection with a control and/or power unit (not shown) which is arranged to provide the power to the electrodes (132a, b; 133a, b) of the mouthpiece 103. The connector 135 may comprise a USB, microUSB, USB-C, FireWire®, Thuderbolt® or any other suitable type of wired connector. The electrical connector or interface 135 is operably connected to the PCBA 141.

In other embodiments, the connector 135 is replaced with a wireless connection means. The wireless connection means may be provided on the PCBA 141 or may be separate therefrom.

In some embodiments, the mouthpiece 103 incorporates a power source, such as a battery. If so, the batter will be operably connected to the PCBA 141.

In use, the mouthpiece 103 is placed in a patient's mouth such that the teach bear on the upper and lower surfaces of the arms 131 and the tongue of the patient is received within the mouthpiece 103 such that the dorsal tongue surface 57 is in contact with the electrodes 132a, b and the sublingual tongue surface is in contact with the electrodes 133a, b. It will be appreciated by those skilled in the art that the electrodes 132a, b will contact a rearward or posterior portion of the dorsal tongue surface 57 and the electrodes 133a, b will contact a frontward or anterior portion of the sublingual tongue surface. With the patient's mouth closed, the flanges 132, 133 are also able to stimulate adjacent muscles on the other side of the tongue, for example the palate muscles. The mouthpiece 103 enables the muscles to be stimulated on both sides of the tongue simultaneously. It will be appreciated that with this design, the muscles based in and around the tongue may be stimulated, including those in hard and soft palate areas.

In order to train the muscles of the mouth, a control unit (not shown) is programmed (or a pre-programmed program is selected) and the mouthpiece 103 and electrodes (132a, b; 133a, b) are connected to the control unit (not shown). Once the program has started, the control unit (not shown) will energise the electrodes according to the required or desired actuation profile to apply the electrical signal to the muscles.

Beneficially, the electrodes (132a, b; 133a, b) will apply an electrical signal to the muscles of the tongue, namely one or more of the mylohyoid, geniohyoid and anterior belly of digastric muscles whilst those of the mouthpiece 103 will apply an electrical signal to the genioglossus muscle and the body of the tongue.

The control unit (not shown) may comprise batteries (not shown) and logic and control circuitry (not shown) to control the application of electric currents to the various electrodes.

Figure 2:
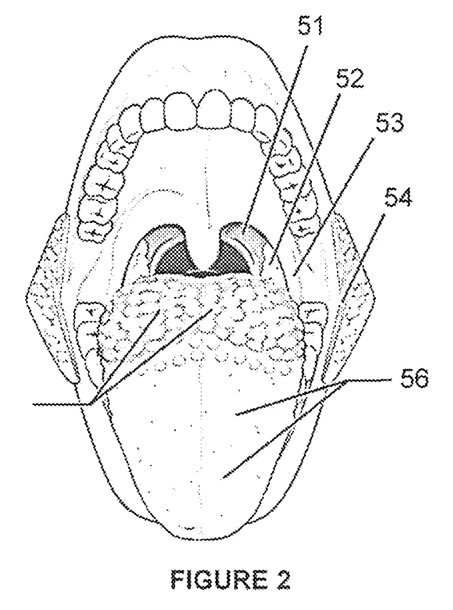
FIG. 2 is a schematic of a human mouth showing the palatoglossus and surface of the tongue.
Figure 3:
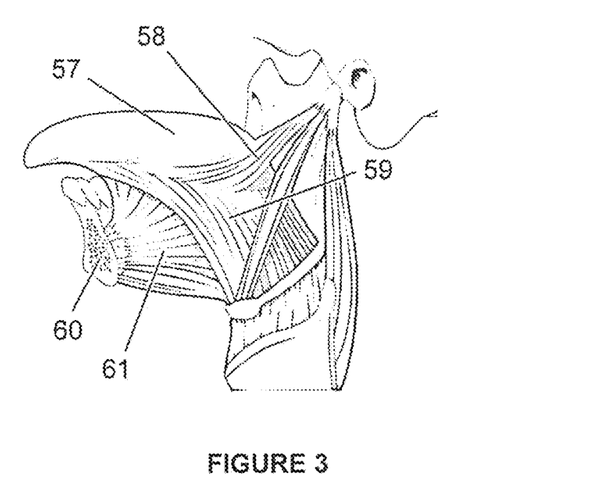
FIG. 3 is a; a schematic illustrating the extrinsic tongue muscles of a human tongue.
Figure 4:
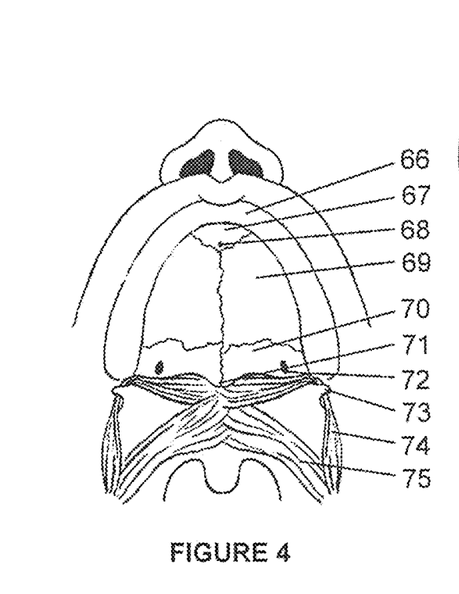
FIG. 4 is a schematic illustrating the intrinsic tongue muscles of a human tongue.

Turning now to FIGS. 2 to 6, there is shown various tongue and palate muscles. Features of the mouth shown in FIGS. 2 to 4 illustrate more clearly the tongue muscles, wherein there is shown the pharyngopalatine arch 51, palatine tonsil 52, palatoglossus 53, buccinator 54, valate papillae 55, fungiform papillae 56, dorsal tongue surface 57, styloglossus 58, hyoglossus 59, mandible bone 60, genioglossus 61, longitudinal, transverse and vertical intrinsic muscles 62, 63, 64 and geniohyoid 65.

It is well established that the tone of the genioglossus muscle 61 most affects the collapsibility of the tongue as it is the biggest of the extrinsic muscle and responsible for pulling the tongue forward and increasing the airway opening in the throat. The tone of intrinsic surface muscles, such as the longitudinal and transverse intrinsic muscles 62, 63, also contribute to the reduction of the collapsibility of the airway.

Figure 5:
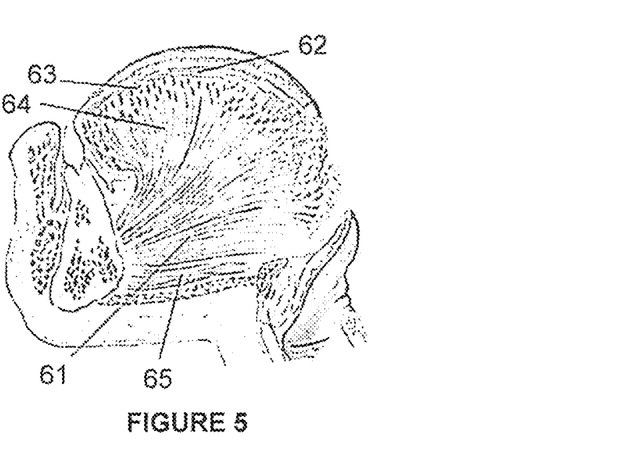
FIG. 5 is another schematic of a human mouth showing the muscles of the palate.
Figure 6:
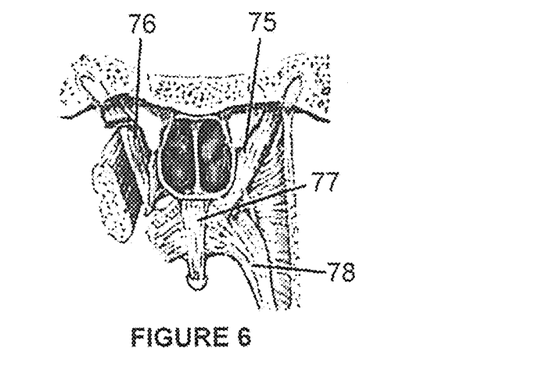
FIG. 6 is a schematic illustrating further muscles of the palate.

Features of the mouth shown in FIGS. 5 and 6 illustrate more clearly the palate muscles, wherein there is shown the dental arch 66, premaxilla 67, incisive foramen 68, palatine process of maxilla 69, palatine bone 70, posterior nasal spine 71, palatine foramen 72, hamulus 73, tensor palatini muscle 74, levator veli palatini muscle 75, tensor veli palatini muscle 76, uvular muscle 77 and palatopharyngeus muscle 78.

To a varying degree, the constrictor and dilator muscles of the palate also contribute to snoring and sleep apnoea. The aim of the treatment is to dilate the throat, hence electrical stimulation is directed at the dilatory palate muscles in the midline, such as the uvular muscle 77, the levator veli palatini muscle 75 and the palatopharyngeus muscle 78.

We have now found that the muscles of the floor of the mouth, and specifically one or more of mylohyoid, geniohyoid and anterior belly of digastric muscles also have an effect on the incidence of sleep apnoea, snoring and SDB in general. We have fund that lateral application of an electrical current across the chin is able to strengthen the muscles of the floor of the mouth which has a surprising and positive effect on muscle tone and helps to further reduce the incidence of SBDs. Indeed, we have found that toning the mylohyoid, and geniohyoid muscles improves the position of the hyoid and hypopharyngeal airway, thereby significantly reducing the incidence of OSA, snoring and SDB in general.

Because of the use of flexible polymeric or plastics materials, the mouthpiece 103 is capable of conforming to the mouth shape of plural users. Further, the use of flexible non-conductive polymeric or plastics materials for the arms ensures said flexibility. By using electrically conductive polymeric or plastics material for at least most of the electric circuitry 140, the flexure of the arms 131 in use will not lead to damage of the electrical circuitry 140. Further, the first flanges 132 and second flanges 133 on which the respective electrodes (132*a, b*; 133*a, b*) are located are also able to flex from their equilibrium position, thereby providing a resilient urging against the tongue of the wearer during use. The use of compatible materials for the mouthpiece arms 131 and electrodes 132*a, b*; 133*a, b* and circuitry 140 ensures that there is no delamination during use, or the material stress does not build up or become established at the interface therebetween.

It will be appreciated by those skilled in the art that several variations to the aforementioned embodiments are envisaged without departing from the scope of the invention. For example, although it is shown that flanges 132, 133 have a respective electrode (132*a, b*; 133*a, b*) protruding proud of a single major surface thereof, this need not be the case. It is envisaged that one or more of the flanges 132, 133 may have a respective electrode protruding proud from both major surfaces thereof, i.e. to increase the area of a user's mouth in contact with the electrodes (132*a, b*; 133*a, b*).

Further, although it is noted that the electrodes (132*a, b*; 133*a, b*) of the mouthpiece 103 are shown as single pads this need not be the case. Instead, they could be multiple pads or contact points.

Although the electrically conductive silicone plastic is described as having silver coated copper granules, it is envisaged that any metal, for example gold, silver or copper or composite material or any other suitable conductive material may be embedded within the silicone matrix. In embodiments, the electrically conductive silicone plastics material may be as described above but with electrically conductive fibres instead of granules. Further, the silicone polymeric or plastics material may be replaced in whole or part by other polymeric or plastics materials.

It will also be appreciated by those skilled in the art that any number of combinations of the aforementioned features and/or those shown in the appended drawings provide clear advantages over the prior art and are therefore within the scope of the invention described herein.

The invention claimed is:

1. A retainer-less device for training oral muscle tone, the device comprising:
   a mouthpiece having a first and second arm extending from a base and diverging away from one another and each carrying at least one electrode on a flange extending from each arm, electrical circuitry operatively connected to said at least one electrode, said at least one electrode configured to direct electrical stimulation to one or more oral muscles, wherein the base is bent and configured to extend over a user's bottom lip, and a connector at a terminal portion of the base that is bent over the user's bottom lip, said connector configured to couple with a control unit, and an encapsulated circuit board assembly within the portion of the base that extends over the user's bottom lip configured to communicate with the control unit to apply an actuation profile to increase oral muscle tone.

2. The device according to claim 1, wherein each of said first and second arms have a longitudinal axis from which the flanges extend as a continuation of the longitudinal axis from a free end of the arm, each flange.

3. A device for training oral muscle tone, the device comprising:
   a retainer-less mouthpiece having joined first and second arms extending from a base and diverging away from one another, each of said first and second arms having a longitudinal axis and having a flange extending as a continuation of the longitudinal axis from a free end of the arm, each flange carrying an at least one electrode, said at least one electrode protruding proud of adjacent portions of the flange, electrical circuitry operatively connected to the electrode, wherein the at least one electrode is configured to electrically stimulate one or more oral muscles of a user, further wherein the base is bent and configured to extend over a user's bottom lip, and a connector at a terminal portion of the base that is bent over the user's bottom lip, the connector configured to couple with a control unit, and an encapsulated circuit board assembly within the portion of the base that extends over the user's bottom lip configured to communicate with the control unit to apply an actuation profile to increase oral muscle tone.

4. The device according to claim 3, wherein the electric circuitry is formed from electrically conductive plastics material or an electrically conductive polymeric material.

5. The device according to claim 4, wherein the electrically conductive polymeric material comprises an electrically conductive silicone plastics material.

6. The device according to claim 4, wherein the electrically conductive polymeric material comprises electrically conductive particles embedded within a polymeric matrix.

7. The device according to claim 3, wherein each of said first and second arms comprises two flanges extending therefrom, each of the flanges comprising a body portion and an electrode protruding proud of the surrounding area of each of the body portions.

8. The device according to claim 7, wherein the electrode of each flange is arranged, in use, to be located or locatable either side of a midline of the face of the user.

9. The device according to claim 7, wherein at least one of said flanges is shaped to cooperate with or approximate or accommodate a sublingual tongue surface.

10. The device according to claim 3, wherein at least one of the flanges is shaped to cooperate with or approximate or accommodate a dorsal tongue surface.

11. The device according to claim 3, wherein the mouthpiece is at least in part formed from a non-electrically conductive polymeric material.

12. The device according to claim 11, wherein the non-electrically conductive polymeric material comprises a silicone rubber.

13. The device according to claim 11, wherein the non-electrically conductive polymeric material at least partially surrounds the at least one electrode and electrical circuitry.

14. The device according to claim 3, wherein the actuation profile comprises an adjustable duration, intensity, frequency or combination thereof, wherein the treatment regime is configured to be adjusted by the user.

* * * * *